Figure 1:
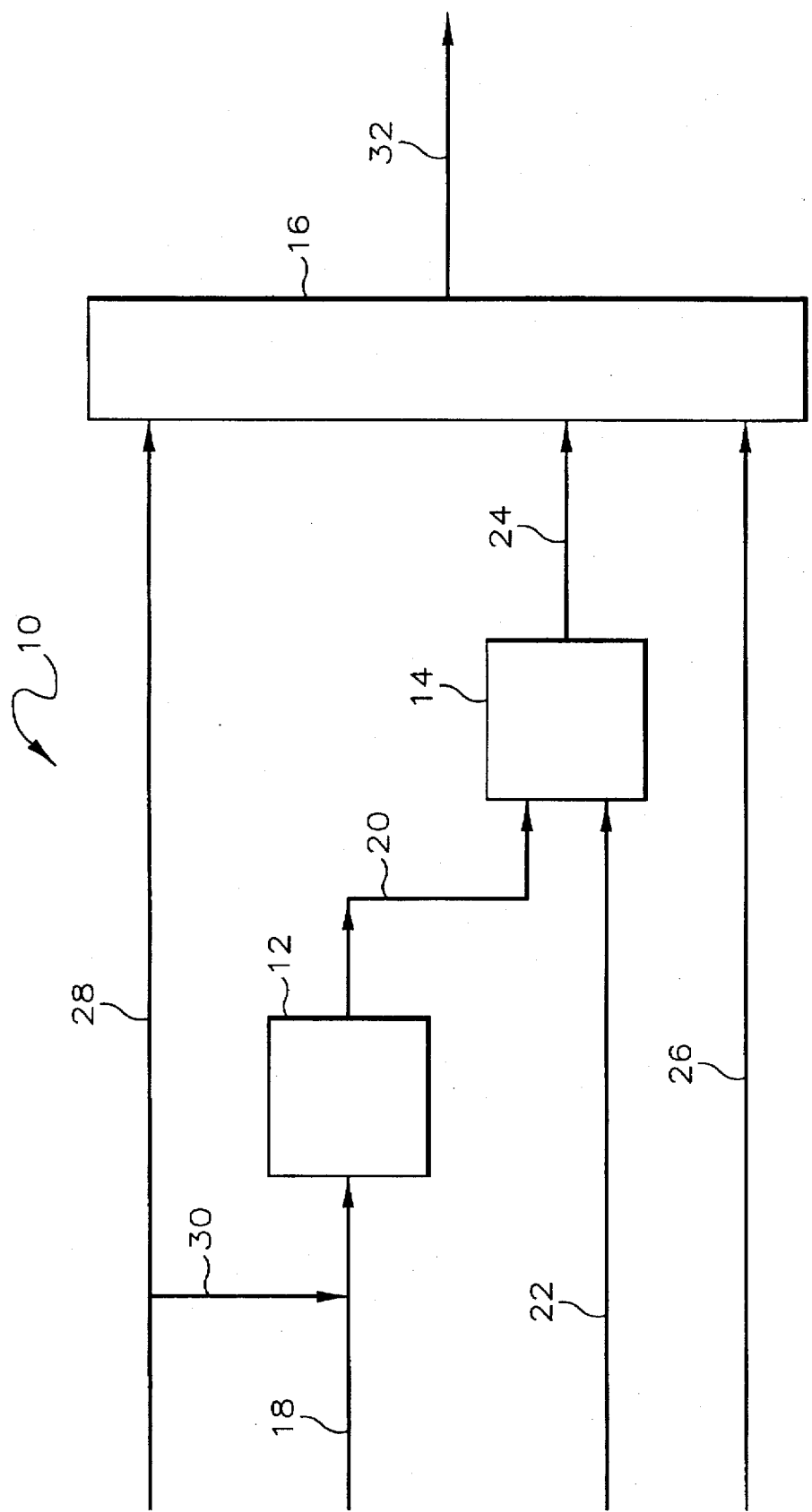

United States Patent [19]
Johnson et al.

[11] Patent Number: 5,684,220
[45] Date of Patent: Nov. 4, 1997

[54] PROCESS FOR REDUCING THE VAPOR PRESSURE OF GASOLINE BY REMOVING AMYLENES THEREFROM AND ENHANCING THE OCTANE THEREOF

[75] Inventors: Marvin M. Johnson; Bruce B. Randolph, both of Bartlesville, Okla.

[73] Assignee: Phillips Petroleum Company, Bartlesville, Okla.

[21] Appl. No.: 410,152

[22] Filed: Mar. 23, 1995

[51] Int. Cl.$^6$ ................................ C07C 2/18; C07C 2/62
[52] U.S. Cl. ......................................... 585/332; 208/71
[58] Field of Search ............................. 585/331, 332; 208/71

[56] References Cited

U.S. PATENT DOCUMENTS

| | | | |
|---|---|---|---|
| 3,662,020 | 5/1972 | Hemminger et al. | 260/683.43 |
| 3,894,931 | 7/1975 | Wace et al. | 208/73 |
| 4,324,938 | 4/1982 | Cosyns et al. | 585/332 |
| 4,367,356 | 1/1983 | Ward | 585/315 |
| 4,393,259 | 7/1983 | Ward et al. | 585/330 |
| 5,237,115 | 8/1993 | Makovec et al. | 585/331 |
| 5,382,744 | 1/1995 | Abbott et al. | 585/709 |
| 5,414,187 | 5/1995 | King et al. | 585/730 |

OTHER PUBLICATIONS

Fieser, et al, Introduction to Organic Chemistry D.C. Heath & Co, Boston 1957 p. 82.

*Primary Examiner*—Gary P. Straub
*Attorney, Agent, or Firm*—Charles W. Stewart

[57] ABSTRACT

A method for reducing the vapor pressure of a gasoline pool by removing amylenes therefrom. The blending octane of gasoline is enhanced by the dimerization of the amylene followed by alkylating the resultant dimate product so as to produce an alkylate end-product that has a higher octane than amylene.

8 Claims, 1 Drawing Sheet

PROCESS FOR REDUCING THE VAPOR PRESSURE OF GASOLINE BY REMOVING AMYLENES THEREFROM AND ENHANCING THE OCTANE THEREOF

This invention relates to a hydrocarbon conversion process. More specifically, the invention is a novel process for reducing the vapor pressure of gasoline by removing amylenes and for enhancing the gasoline octane by further processing of the amylenes to produce a gasoline blending component.

Government regulations are increasingly requiring the removal of olefin compounds from gasoline and the limiting of gasoline vapor pressure. Efforts to remove amylene olefin compounds from a gasoline pool, however, pose numerous problems. On particular problem relates to finding some other use of the amylenes removed from the gasoline pool. One use for such amylenes can be as an alkylation reaction feed material This use, however, itself creates problems. For example, an amylene alkylate can be an inferior alkylate to other forms of alkylate, particularly, a butylene alkylate, and it can have a lower octane value than some amylene olefins. Also, synthetic isopentane is formed during the alkylation of amylene olefin compounds. Traditionally, the production of synthetic isopentane has not been much of a concern; but, instead, it has been desirable because of the relatively high octane value of isopentane. However, due to the aforementioned regulatory changes, which require a lower gasoline vapor pressure than previously allowed, it is undesirable to increase the amount of isopentane in the gasoline pool. The formation of synthetic isopentane during the catalytic alkylation of amylene offsets some of the benefits that result from the alkylation of amylene removed from the gasoline pool by increasing the vapor pressure thereof.

It is an object of this invention to provide a method for removing olefins, particularly amylenes, from a gasoline pool.

A further object of this invention is to convert amylenes removed from a gasoline pool into a suitably high octane gasoline blending component.

A still further object of this invention is to lower the vapor pressure of a gasoline pool by removing amylenes therefrom.

A yet further object of this invention is to enhance the octane of a gasoline pool by converting the amylenes removed therefrom into a gasoline product having a higher octane than the amylenes thus removed from the gasoline pool.

The invention is a method for converting an amylene feedstock into a high octane gasoline blend stock. The amylene feedstock is contacted with a dimerization catalyst, contained in a dimerization reaction zone, under suitable dimerization reaction conditions to thereby produce a dimate. The dimate is contacted with an alkylation catalyst, contained in an alkylation reaction zone, under suitable alkylation reaction conditions to thereby produce the high octane gasoline blend stock.

Another embodiment of the invention includes a hydrocarbon conversion process, which includes an alkylation process system having an alkylation reaction zone and a gasoline pool containing amylenes. The hydrocarbon conversion process is improved by removing a portion of the amylenes contained in the gasoline pool and processing further such removed amylenes. The removed portion of amylenes are contacted with a dimerization catalyst, contained in a dimerization zone, under suitable dimerization reaction conditions to produce a dimate. The dimate is contacted with an alkylation catalyst within the alkylation reaction zone under suitable alkylation reaction conditions to produce an alkylate product. The alkylate product is passed to the gasoline pool.

In the accompanying drawing:

FIG. 1 is a schematic representation of the overall process system related to the inventive method.

Other objects and advantages of the invention will be apparent from the following detailed description of the invention and the appended claims thereof.

The inventive hydrocarbon conversion process provides for the production of a suitably high octane gasoline blending component through the use of two different reactions with two separate reaction zones. The two reaction zones are a dimerization zone and an alkylation zone. The two reaction zones are integrated in such a manner as to permit the processing of amylene hydrocarbons to produce a high octane gasoline blending component.

Amylene compounds are generally found as a component of a typical refinery gasoline pool. The source of such amylenes is usually the cracked product from a conventional fluidized catalytic cracker (FCC) operation. In the typical FCC operation, there is an FCC debutanizer used for fractionating an FCC cracked hydrocarbon stream with a bottoms stream, comprising hydrocarbons having at least five (5) carbon atoms, passing to a gasoline pool and an overhead stream, comprising hydrocarbons having less than five (5) carbon atoms, undergoing further processing. Amylenes removed from the bottoms stream of the FCC debutanizer or, ultimately, from the FCC cracked hydrocarbon stream can be utilized as an amylene feedstock, containing amylenes, to the dimerization reaction zone of the inventive two-reaction step process.

Amylenes can be removed from the gasoline pool by any suitable approach or more commonly by separation from an FCC gasoline stream prior to passing such stream to the gasoline pool. One approach to processing amylenes not passed to the gasoline pool is to use them as an alkylation reaction feed whereby amylenes are catalytically reacted with isoparaffins, in the presence of an alkylation catalyst such as hydrogen fluoride (HF) and sulfuric acid, to form an amylene alkylate product. The conventional alkylation of amylenes, however, can provide an alkylate product that is an inferior gasoline blending component than the amylene itself. Also, the alkylation of amylenes result in the simultaneous production of undesirable synthetic isopentane. The inventive two-reaction step process provides means by which the amylenes removed from the gasoline pool can be processed to give a gasoline blending product generally having an octane value approximately equal to, or possibly exceeding, that of the amylene but without producing the undesirable quantities of synthetic isopentane associated with the alkylation of amylene.

In the first step of the inventive process, a feed stream, comprising amylene, is passed or charged to a dimerization reaction zone which contains a dimerization catalyst and is operated at conditions suitable for promoting the dimerization reaction.

Suitable dimerization reaction conditions for the dimerization of amylene include a broad range of suitable dimerization reaction pressures from about 15 psig to about 1200 psig with a preferred dimerization reaction pressure range of from about 50 psig to about 1100 psig. Most preferably, the dimerization reaction pressure can range from 75 psig to 1000 psig. The dimerization reaction temperature maintained in the dimerization reaction zone can be in the range of from about 100° F. to about 800° F. with a preferred dimerization reaction temperature being in the range of from about 150° F. to about 750° F. Most preferably, the dimerization reaction temperature is in the range of from 200° F. to 600° F.

Any suitable dimerization catalyst may be employed in the inventive process provided that it provides for the dimerization of amylene. The preferred dimerization catalyst to be used in the dimerization zone is a solid phosphoric acid catalyst. A solid phosphoric acid catalyst is a solid catalyst comprising a siliceous material of high adsorption capacity impregnated with an acid of phosphorus such as an ortho-, pyro-, or tetra-phosphoric acid. Specific examples of such solid phosphoric acid catalyst include phosphoric acid on kieselguhr or on silica or on quartz.

The effluent from the dimerization reaction zone contains a dimer product, or dimate, comprising a mixture of olefins having from five to eleven carbon atoms. The major component of the dimate includes olefins having from nine to eleven carbon atoms.

The alkylation process contemplated by the present invention is a liquid phase process wherein mono-olefin hydrocarbons such as propylene, butylenes, pentylenes (amylenes), hexylenes, heptylenes, octylenes and the like are alkylated in the presence of an alkylation catalyst, such as hydrogen fluoride and sulfuric acid, but preferably, hydrogen fluoride, by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate product comprising a major portion of highly branched, high octane value aliphatic hydrocarbons having at least seven carbon atoms and less than ten carbon atoms.

In the inventive process, the dimate from the dimerization reaction zone is charged to the alkylation reaction zone of the alkylation process system wherein it is contacted with the alkylation catalyst contained therein. Within the alkylation reaction zone, suitable alkylation reaction conditions are maintained. The alkylate product produced from the alkylation reaction zone is passed to a gasoline pool where it is used as a blending component in the manufacture of a gasoline end-product for introduction into the marketplace.

In order to improve selectivity of the alkylation reaction toward the production of the desirable highly branched aliphatic hydrocarbons having seven or more carbon atoms, a substantial stoichiometric excess of isoparaffin hydrocarbon is desirable in the alkylation reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8.5 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better alkylate quality.

Alkylation reaction temperatures within the contemplation of the present invention are generally in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone in the presence of an alkylation catalyst of the present invention should generally be sufficient to provide essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin can be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and with&am from the reaction system while the partially spent catalyst is recycled to the reactor. If desired, a portion of the catalyst can be continuously regenerated or reactivated by any suitable treatment and returned to the alkylation reactor.

The dimate alkylate produced by the inventive two-reaction step process is a more desirable gasoline blending component than an amylene alkylate produced by the catalyzed alkylation of an amylene feedstock. The dimerization of an amylene feedstock to produce a dimate product followed by alkylation of the dimate product to produce an alkylate product, or dimate alkylate, provides a gasoline blending component that has a higher blending octane value than that of an amylene alkylate. The dimate alkylate has an octane value that is greater than an amylene alkylate due to a greater concentration of hydrocarbons having eight carbon atoms and, in particular, a greater concentration of trimethylpentane.

Another benefit of the inventive two-reaction step process is that the synthetic isopentane produced is less than that produced in the direct alkylation of an amylene feedstock. The combination of the removal of amylenes from a gasoline pool and the inventive two-reaction step processing of such removed amylenes provides for a gasoline pool having a reduced vapor pressure and an improved overall octane. The dimate alkylate provides a high octane blend stock having an octane value, defined as the sum of the research octane and motor octane divided by two, exceeding about 88.0 and, preferably, exceeding about 89.0. Most preferably, the octane value of the dimate alkylate can exceed 90.0.

Now referring to FIG. 1, there is presented a schematic flow diagram of an overall process system 10, which includes a dimerization reaction zone 12, an alkylation reaction zone 14, and a gasoline pool 16.

An amylene feedstock passes to dimerization reaction zone 12 by way of conduit 18. Within dimerization reaction zone 12 the amylenes contained in the amylene feedstock undergo a catalyzed dimerization reaction whereby a dimate product is produced.

The dimate product passes from dimerization reaction zone 12 by way of conduit 20 to alkylation reaction zone 14. Isobutane feed is charged to alkylation zone 14 through conduit 22. Within alkylation reaction zone 14, the dimate product is contacted with an alkylation catalyst contained therein under suitable alkylation reaction conditions to thereby produce an alkylate product.

The alkylate product from alkylation reaction zone 14 passes by way of conduit 24 to gasoline pool 16. Other gasoline blending components can pass to gasoline pool 16 by way of conduit 26. Additionally, a product stream containing amylene compounds can pass to gasoline pool 16 by way of conduit 28. Blended gasoline passes into the commercial marketplace by way of conduit 32.

A portion of the amylenes in the product stream which passes by way of conduit 28 to gasoline pool 16 can be removed from the gasoline pool by way of diverting such flow through conduit 30 to dimerization reaction zone 12. The diversion or removal of a portion of the amylenes previously contained in gasoline pool 16 provides for a reduction in the vapor pressure of the gasoline pool. The dimerization of amylene compounds followed by alkylation of the dimate product provides an alkylate product having a higher octane number than that of the amylenes previously contained in the gasoline pool. Thus, a dual benefit of reducing the vapor pressure of the gasoline pool and enhancing its overall octane value are achieved through the removal of amylene from such gasoline pool.

The following examples demonstrate the advantages of the present invention. The example is by way of illustration only, and is not intended as a limitation upon the invention as set out in the appended claims.

EXAMPLE I

This example describes the experimental procedure used to alkylate a mixed amylene feed and a dimate feed. A comparison of the amylene alkylate to the dimate alkylate produced by the inventive two reaction step process is provided.

An appropriately equipped 300 mL Monel autoclave was charged with 75 g HF containing 2% $H_2O$ and about 1% soluble hydrocarbons. After heating to obtain an acid temperature of 90°–100° F., a 24 g feed sample was introduced at a rate of approximately 60 g/minute, while the reactor contents were stirred at 1500 rpm. After a 5 minute contact time, the contents of the reactor were transferred to a monel sight gauge. When the acid and hydrocarbon product phases were separated, the hydrocarbon product was collected in a stainless steel bomb, passed over $Al_2O_3$ beads and collected in a second stainless steel bomb. The scrubbed product was analyzed by gas chromatography. The gas chromatograph oven conditions and column were chosen so as to achieve complete separation of components from $C_3$ through $C_9$.

The feed mixtures consisted of mixed amylenes (branched and linear isomers) or an amylene dimate prepared as described above, using phosphoric acid on Kieselguhr as a catalyst, diluted with isobutane to get an isobutane/olefin ratio of 11–13 by weight.

The results presented in Table I show that the dimate alkylate has a higher octane value than the amylene alkylate. Also, synthetic isopentane produced during the alkylation of the dimate is significantly less than the synthetic isopentane produced during the alkylation of a mixed amylene feed. Furthermore, the concentration of components having eight or more carbon atoms is greater in the dimate alkylate than in the amylene alkylate.

TABLE I

Results From the Batch Alkylation of a Mixed Amylene Feed and a Dimate Feed

| Feed Type | Mixed Amylene | Dimate |
| --- | --- | --- |
| Rxtr Type | Batch | Batch |
| Temp., °F. | 90 | 103 |
| Feed | ~13 | 11.5 |
| Acid:Hydrocarbon | 3.6 | 3.9 |
| Conv., % | 100.0 | 100.0 |
| IC5 Selec, % | 60.9 | 43.2 |
| C5+ Liquid Product (Normalized to iC4) | | |
| Lights | 3.03 | 8.07 |
| IC5 | 34.84 | 13.08 |
| NC5 | 8.96 | 0.32 |
| C6 | 0.90 | 5.15 |
| C7 | 0.67 | 2.64 |
| C8 | 31.11 | 41.14 |
| C9+ | 20.34 | 29.48 |
| TMP's | 28.40 | 35.89 |
| T/D | 10.90 | 7.00 |
| R + M/2(c) | 88.80 | 90.10 |

IC50 Selec = Isopentane Selectivity, as a % of $C_5$ olefin
Dimate = Mixture of C5, C6, C7, C8, C9, C10, C11 olefins
Lights = $C_3$, $nC_4$
(c) = calculated from gas chromatography results While this invention has been described in terms of the presently preferred embodiment, reasonable variations and modifications are possible by those skilled in the art. Such variations and modifications are within the scope of the described invention and the appended claims.

That which is claimed is:

1. In a hydrocarbon conversion process which includes an alkylation process system having an alkylation reaction zone and a gasoline pool containing amylenes, the improvement comprises:

removing a portion of the amylenes contained in said gasoline pool;

contacting said portion of the amylenes contained in said gasoline pool with a solid phosphoric acid dimerization catalyst contained in a dimerization reaction zone under suitable dimerization reaction conditions to thereby produce a dimate, wherein said suitable dimerization reaction conditions include a dimerization reaction pressure in the range of from about 15 psig to about 1200 psig and a dimerization reaction temperature in the range of from about 100° F. to about 800° F.;

contacting said dimate and isobutane with an alkylation catalyst, comprising hydrogen fluoride, within said alkylation reaction zone under suitable alkylation reaction conditions to thereby produce an alkylate product having a research octane value exceeding about 89.0 and less synthetic isopentane than that which would be produced in the direct alkylation of said portion of amylenes, wherein said suitable alkylation reaction conditions include an alkylation reaction pressure in the range of from about 40 psig to about 160 psig and an alkylation reaction temperature in the range of from about 0° F. to about 150° F.; and passing said alkylate product to said gasoline pool.

2. A hydrocarbon conversion process as recited in claim 1, wherein said dimate comprises a mixture of olefins having from five to eleven carbon atoms.

3. A hydrocarbon conversion process as recited in claim 1, wherein said suitable dimerization reaction conditions include a dimerization reaction pressure in the range of from about 50 psig to about 1100 psig and a dimerization reaction temperature in the range of from about 150° F. to about 750° F.; wherein said dimate comprises a mixture of olefins having from five to eleven carbon atoms; wherein said suitable alkylation reaction conditions include an alkylation reaction pressure in the range of from about 40 psig to about 160 psig and an alkylation temperature in the range of from about 30° F. to about 130° F.; and wherein said alkylate product has a research octane value exceeding 90.0.

4. A hydrocarbon conversion process as recited in claim 3, wherein said dimate comprises a mixture of olefins having from five to eleven carbon atoms.

5. A method for converting an amylene feedstock, containing amylenes, into a high octane gasoline blend stock, said method comprises the steps of:

contacting said amylene feedstock with a solid phosphoric acid dimerization catalyst contained in a dimerization reaction zone under suitable dimerization reaction conditions to thereby produce a dimate, wherein said suitable dimerization reaction conditions include a dimerization reaction pressure in the range of from about 15 psig to about 1200 psig and a dimerization reaction temperature in the range of from about 100° F. to about 800° F.; and contacting said dimate and isobutane with an alkylation catalyst, comprising hydrogen fluoride, contained within an alkylation reaction zone under suitable alkylation reaction conditions to thereby produce said high octane gasoline blend stock having a research octane value exceeding about 89.0 and less synthetic isopentane than that which would be produced in the direct alkylation of said amylene feedstock, wherein said suitable alkylation reaction conditions include an alkylation reaction pressure in the range of from about 40 psig to about 160 psig and an alkylation reaction temperature in the range of from about 0° F. to about 150° F.

6. A hydrocarbon conversion process as recited in claim 5, wherein said dimate comprises a mixture of olefins having from five to eleven carbon atoms.

7. A hydrocarbon conversion process as recited in claim 5, wherein said suitable dimerization reaction conditions include a dimerization reaction pressure in the range of from about 50 psig to about 1100 psig and a dimerization reaction temperature in the range of from about 150° F. to about 750° F.; wherein said dimate comprises a mixture of olefins having from five to eleven carbon atoms; wherein said suitable alkylation reaction conditions include an alkylation reaction pressure in the range of from about 40 psig to about 160 psig and an alkylation temperature in the range of from about 30° F. to about 130° F.; and wherein said high octane gasoline blend stock having a research octane value exceeding 90.0.

8. A hydrocarbon conversion process as recited in claim 7 wherein said dimate comprises a mixture of olefins having from five to eleven carbon atoms.

* * * * *